United States Patent [19]

Frisch

[11] Patent Number: 5,776,743
[45] Date of Patent: Jul. 7, 1998

[54] METHOD OF SENSITIZING TUMOR CELLS WITH ADENOVIRUS E1A

[75] Inventor: Steven M. Frisch, Del Mar, Calif.

[73] Assignee: La Jolla Cancer Research Foundation, La Jolla, Calif.

[21] Appl. No.: 301,316

[22] Filed: Sep. 6, 1994

[51] Int. Cl.$^6$ .................. C12N 5/10; C12N 5/08; C12N 5/22
[52] U.S. Cl. .................. 435/172.3; 935/57; 935/71; 935/32; 536/23; 536/72; 435/325; 435/363; 435/366; 435/367; 435/368; 435/369; 435/370; 435/371; 435/371.1; 435/371.2; 435/371.3; 435/235.1; 424/93.1; 424/93.2; 424/93.21; 514/44
[58] Field of Search ................ 514/44; 435/172.3, 435/240.1, 240.2, 320.1, 325, 363, 366, 367, 368, 369, 370, 371, 372, 372.1, 372.2, 372.3, 235.1; 424/93.1, 93.2, 93.21; 536/23.72; 935/57, 71, 32

[56] References Cited

U.S. PATENT DOCUMENTS 5,516,631  5/1996  Frisch .................................. 435/69.1

FOREIGN PATENT DOCUMENTS

WO 94/18992  9/1994  WIPO.

OTHER PUBLICATIONS

Orkin et al. "Report and Recomendations... Gene Therapy." Dec. 7,1995 pp. 1–40. NIH.
Blaese M. et al. Cancer Gene Therapy 2(4): 291–297 (1995).
Culver, K.W. et al. "Gene Therapy for Cancer". Trends in Genetics 10(5). May 1994, pp. 174–178.
Brown, D. The Washington Post. Dec. 8, 1995. pp. A1, A22.
Marshall, E. Science 269: 1050–1055 (1995).
Yu et al., "Adenovirus type E1A gene products act as transformation suppressors of the neu oncogene." *Molec. Cell. Biol.*11:1745–1750 (1991).
Miller et al., "Improved retroviral vectors for gene transfer and expression."*Biotechniques*7:980–990 (1989).
Yu et al., "Reexpression of neu–encoded oncoprotein counteracts the tumor–suppressing but not the metastasis–suppressing function of E1A."*Cancer Research*53:5784–5790 (1993).
Fujiwara et al., "Induction of chemosensitivity in human lung cancer cells in vivo by adenovirus–mediated transfer of the wild–type p53 gene."*Cancer Research*54:2287–2291 (1994).
Matsuzaki et al., "Mechanism of selective killing by dilinoleoylglycerol of cells transformed by the E1A gene of adenovirus type 12."*Cancer Research*49:5702–5707 (1989).
Cook et al., "E1A oncogene expression level in sarcoma cells: an indepedent determinant of cytolytic susceptibility and tumor rejection."*Oncogene*8:625–635 (1993).
Cook et al., "Expression of the adenovirus E1A oncogene during cell transformation is sufficient to induce susceptibility to lysis by host inflammatory cells."*Proc. Natl. Acad. Sci USA*83:6965–6969 (1986).

Cook et al., "Adenovirus E1A gene induction of susceptibility to lysis by natural killer cells and activated macrophages in infected rodent cells."*J. of Virology*61(11):3510–3520 (1987).
Cook et al., "Differential induction of cytolytic susceptibility by E1A, myc, and ras oncogenes in immortalized cells."63(8) :3408–3415 (1989).
Cook et al., "Role of tumor necrosis factor–αin E1A oncogene–induced susceptibility of neoplastic cells to lysis by natural killer cells and activated macrophages."*J. of Immunology* 142 4527–4534 (1989).
Duerksen–Hughes et al., "Adenovirus E1A renders infected cells sensitive to cytolysis by tumor necrosis factor. "*J. of Immunology*143:4193–4200 (1989).
Walker et al., "E1A oncogene induction of cytolytic susceptibility eliminates sarcoma cell tumorigenicity."*Proc. Natl. Acad. Sci. USA*88:6491–6495 (1991).
Frisch Steven M., "Antioncogenic effect of adenovirus E1A in human tumor cells."*Proc. Natl. Acad. Sci. USA*,88:9077–9081 (1991).
Frisch and Francis, "Disruption of epithelial cell–matrix interactions induces apoptosis."*J. Cell. Biol.*, 124(4):619–626 (1994).
Lowe et al., "p53–Dependent apoptosis modulates the cytotoxicity of anticancer agents."*Cell*, 74:957–967 (1993).
Rao et al., "The adenovirus E1A proteins induce apoptosis, which is inhibited by the E1B 19–kDa and Bcl–2 proteins."*Proc.Natl. Acad. Sci. USA*,89:7742–7746 (1992).
Evan et al., "Induction of apoptosis in fibroblasts by c–myc protein."*Cell*,69:119–128 (1992).
Chen et al., "Induction by E1A oncogene expression of cellular susceptibility to lysis by TNF."*Nature*,330:581–583 (1987).
Fanidi et al., "Cooperative interaction between c–myc and bcl–2 proto–oncogenes."*Nature*,359:554–556 (1992).
Sanchez–Prieto et al., "Modulation of cellular chemoresistance in keratinocytes by activation of different oncogenes."*Int. J. Cancer*,60:235–243 (1995).

(List continued on next page.)

*Primary Examiner*—Christopher S. F. Low
*Attorney, Agent, or Firm*—Campbell & Flores LLP

[57] ABSTRACT

The present invention is directed to methods of sensitizing a human tumor cell with adenovirus E1A. The methods involve treating a human tumor cell by, first, introducing into the tumor cell nucleic acid encoding a polypeptide having adenovirus E1A activity, expressing the E1A active polypeptide in the cell, and then either contacting the E1A expressing tumor cell with a chemotherapeutic agent or irradiating the E1A-expressing tumor cell. The invention also provides methods of enhancing a subject's response to chemotherapy or irradiation by introducing into a subject's tumor cells nucleic acid encoding a polypeptide having adenovirus E1A activity, expressing the E1A active polypeptide in the cells and finally, administering either a chemotherapeutic agent or irradiation. The invention also provides a method of treating cancer.

7 Claims, 7 Drawing Sheets

OTHER PUBLICATIONS

Gruber and Greil, "Apoptosis and therapy of malignant diseases of the hematopoietic system."*Int. Arch. Allergy Immunol.*,105:368–373 (1994).

Sinkovics and Horvath, "Apoptosis by Genetic Engineering."*Leukemia,*8:S98–S102 (1994).

Canman and Kastan, "Induction of apoptosis by tumor suppressor genes and oncogenes."*Cancer Biol.*,6:17–25 (1995).

Martin and Green, "Apoptosis as a goal of cancer therapy."*Current Opinion in Oncology,* 6:616–621 (1994).

```
GGACTGAAA ATG AGA CAT ATT ATC TGC CAC GGA GGT GTT ATT ACC GAA    48
          Met Arg His Ile Ile Cys His Gly Gly Val Ile Thr Glu
          1               5                   10

GAA ATG GCC GCC AGT CTT TTG GAC CAG CTG ATC GAA GAG GTA CTG GCT    96
Glu Met Ala Ala Ser Leu Leu Asp Gln Leu Ile Glu Glu Val Leu Ala
            15                  20                  25

GAT AAT CTT CCA CCT CCT AGC CAT TTT GAA CCA CCT ACC CTT CAC GAA   144
Asp Asn Leu Pro Pro Pro Ser His Phe Glu Pro Pro Thr Leu His Glu
        30                  35                  40              45

CTG TAT GAT TTA GAC GTG ACG GCC CCC GAA GAT CCC AAC GAG GAG GCG   192
Leu Tyr Asp Leu Asp Val Thr Ala Pro Glu Asp Pro Asn Glu Glu Ala
            50                  55                  60

GTT TCG CAG ATT TTT CCC GAC TCT GTA ATG TTG GCG GTG CAG GAA GGG   240
Val Ser Gln Ile Phe Pro Asp Ser Val Met Leu Ala Val Gln Glu Gly
        65                  70                  75

ATT GAC TTA CTC ACT TTT CCG CCG CCC GGT TCT CCG GAG CCG CCT CCT   288
Ile Asp Leu Leu Thr Phe Pro Pro Pro Ala Pro Gly Ser Pro Glu Pro Pro
            80                  85                  90
```

FIG. 5A

```
CAC CTT TCC CGG CAG CCC GAG CAG CCG GAG CAG AGA GCC TTG GGT CCG       336
His Leu Ser Arg Gln Pro Glu Gln Pro Glu Gln Arg Ala Leu Gly Pro
 95                         100                 105

GTT TCT ATG CCA AAC CTT GTA CCG GAG GTG ATC GAT CTT ACC TGC CAC       384
Val Ser Met Pro Asn Leu Val Pro Glu Val Ile Asp Leu Thr Cys His
        110                 115                 120             125

GAG GCT GGC TTT CCA CCC AGT GAC GAC GAT GAA GAG GGT                   426
Glu Ala Gly Phe Pro Pro Ser Asp Asp Asp Glu Glu Gly
            130                 135

GAGGAGTTTG TGTTAGATTA TGTGGAGCAC CCCGGGCACG GTTGCAGGTC TTGTCATTAT     486
GluGluPheV alLeuAspTy rValGluHis ProGlyHisG lyCysArgSe rCysHisTyr

CACCGGAGGA ATACGGGGGA CCCAGATATT ATGTGTTCGC TTTGCTATAT GAGGACCTGT     546
HisArgArgA snThrGlyAs pProAspIle MetCysSerL euCysTyrMe tArgThrCys

GGCATGTTTG TCTACAGTAA GTGAAAATTA TGGGCAGTGG GTGATAGAGT GGTGGGTTTG     606
GlyMetPheV alTyrSer

GTGTGGTAAT TTTTTTTTTA ATTTTTACAG TTTTGTGGTT TAAAGAATTT TGTATTGTGA     666

TTTTTTTAAA AGGT CCT GTG TCT GAA CCT GAG CCC GAG CCT GAG CCA GAA       716
          Pro Val Ser Glu Pro Glu Pro Glu Pro Glu Pro Glu
          140                 145                 150
```

FIG.5B

```
CCG GAG CCT GCA AGA CCT ACC CGC CGT CCT AAA ATG GCG CCT GCT ATC        764
Pro Glu Pro Ala Arg Pro Thr Arg Arg Pro Lys Met Ala Pro Ala Ile
155                 160                 165

CTG AGA CGC CCG ACA TCA CCT GTG TCT AGA GAA TGC AAT AGT AGT ACG        812
Leu Arg Arg Pro Thr Ser Pro Val Ser Arg Glu Cys Asn Ser Ser Thr
170                 175                 180

GAT AGC TGT GAC TCC GGT CCT TCT AAC ACA CCT CCT GAG ATA CAC CCG        860
Asp Ser Cys Asp Ser Gly Pro Ser Asn Thr Pro Pro Glu Ile His Pro
185                 190                 195

GTG GTC CCG CTG TGC CCC ATT AAA CCA GTT GCC AGA GTT GGT GGG            908
Val Val Pro Leu Cys Pro Ile Lys Pro Val Ala Arg Val Gly Gly
200                 205                 210                 215

CGT CGC CAG GCT GTG GAA TGT ATC GAG GAC TTG CTT AAC GAG CCT GGG        956
Arg Arg Gln Ala Val Glu Cys Ile Glu Asp Leu Leu Asn Glu Pro Gly
220                 225                 230

CAA CCT TTG GAC TTG AGC TGT AAA CGC CCC AGG CCATAAGGTG T              1000
Gln Pro Leu Asp Leu Ser Cys Lys Arg Pro Arg Pro
235                 240
```

FIG.5C

SEQUENCE LISTING ( 1 ) GENERAL INFORMATION:

( i i i ) NUMBER OF SEQUENCES: 4

( 2 ) INFORMATION FOR SEQ ID NO:1:

( i ) SEQUENCE CHARACTERISTICS:
  ( A ) LENGTH: 1000 base pairs
  ( B ) TYPE: nucleic acid
  ( C ) STRANDEDNESS: both
  ( D ) TOPOLOGY: linear ( i i ) MOLECULE TYPE: cDNA ( i i i ) HYPOTHETICAL: NO ( i v ) ANTI-SENSE: NO ( i x ) FEATURE:
  ( A ) NAME/KEY: CDS
  ( B ) LOCATION: join(10..426, 681..993)
  ( D ) OTHER INFORMATION: /note= "This protein is the product of alternative splicing of the precursor RNA such that protein in this form is a subset of the larger E1A protein as shown in SEQ ID NOS: 3-4."

( x i ) SEQUENCE DESCRIPTION: SEQ ID NO:1:

```
GGACTGAAA  ATG AGA CAT ATT ATC TGC CAC GGA GGT GTT ATT ACC GAA              48
           Met Arg His Ile Ile Cys His Gly Gly Val Ile Thr Glu
            1               5                  10

GAA ATG GCC GCC AGT CTT TTG GAC CAG CTG ATC GAA GAG GTA CTG GCT             96
Glu Met Ala Ala Ser Leu Leu Asp Gln Leu Ile Glu Glu Val Leu Ala
     15                  20                  25

GAT AAT CTT CCA CCT CCT AGC CAT TTT GAA CCA CCT ACC CTT CAC GAA            144
Asp Asn Leu Pro Pro Pro Ser His Phe Glu Pro Pro Thr Leu His Glu
 30                  35                  40                  45

CTG TAT GAT TTA GAC GTG ACG GCC CCC GAA GAT CCC AAC GAG GAG GCG            192
Leu Tyr Asp Leu Asp Val Thr Ala Pro Glu Asp Pro Asn Glu Glu Ala
                 50                  55                  60

GTT TCG CAG ATT TTT CCC GAC TCT GTA ATG TTG GCG GTG CAG GAA GGG            240
Val Ser Gln Ile Phe Pro Asp Ser Val Met Leu Ala Val Gln Glu Gly
             65                  70                  75

ATT GAC TTA CTC ACT TTT CCG CCG GCG CCC GGT TCT CCG GAG CCG CCT            288
Ile Asp Leu Leu Thr Phe Pro Pro Ala Pro Gly Ser Pro Glu Pro Pro
         80                  85                  90

CAC CTT TCC CGG CAG CCC GAG CAG CCG GAG CAG AGA GCC TTG GGT CCG            336
His Leu Ser Arg Gln Pro Glu Gln Pro Glu Gln Arg Ala Leu Gly Pro
     95                 100                 105

GTT TCT ATG CCA AAC CTT GTA CCG GAG GTG ATC GAT CTT ACC TGC CAC            384
Val Ser Met Pro Asn Leu Val Pro Glu Val Ile Asp Leu Thr Cys His
110                 115                 120                 125

GAG GCT GGC TTT CCA CCC AGT GAC GAC GAG GAT GAA GAG GGT                    426
Glu Ala Gly Phe Pro Pro Ser Asp Asp Glu Asp Glu Glu Gly
                130                 135

GAGGAGTTTG TGTTAGATTA TGTGGAGCAC CCCGGGCACG GTTGCAGGTC TTGTCATTAT          486

CACCGGAGGA ATACGGGGGA CCCAGATATT ATGTGTTCGC TTTGCTATAT GAGGACCTGT          546

GGCATGTTTG TCTACAGTAA GTGAAAATTA TGGGCAGTGG GTGATAGAGT GGTGGGTTTG          606

GTGTGGTAAT TTTTTTTTTA ATTTTACAG TTTTGTGGTT TAAAGAATTT TGTATTGTGA           666

TTTTTTTAAA AGGT CCT GTG TCT GAA CCT GAG CCT GAG CCC GAG CCA GAA            716
                Pro Val Ser Glu Pro Glu Pro Glu Pro Glu Pro Glu
                140                 145                 150

CCG GAG CCT GCA AGA CCT ACC CGC CGT CCT AAA ATG GCG CCT GCT ATC            764
Pro Glu Pro Ala Arg Pro Thr Arg Arg Pro Lys Met Ala Pro Ala Ile
                155                 160                 165

CTG AGA CGC CCG ACA TCA CCT GTG TCT AGA GAA TGC AAT AGT AGT ACG            812
Leu Arg Arg Pro Thr Ser Pro Val Ser Arg Glu Cys Asn Ser Ser Thr
         170                 175                 180

GAT AGC TGT GAC TCC GGT CCT TCT AAC ACA CCT CCT GAG ATA CAC CCG            860
Asp Ser Cys Asp Ser Gly Pro Ser Asn Thr Pro Pro Glu Ile His Pro
```

-continued

```
              185                          190                         195
GTG  GTC  CCG  CTG  TGC  CCC  ATT  AAA  CCA  GTT  GCC  GTG  AGA  GTT  GGT  GGG         908
Val  Val  Pro  Leu  Cys  Pro  Ile  Lys  Pro  Val  Ala  Val  Arg  Val  Gly  Gly
200                      205                     210                     215

CGT  CGC  CAG  GCT  GTG  GAA  TGT  ATC  GAG  GAC  TTG  CTT  AAC  GAG  CCT  GGG         956
Arg  Arg  Gln  Ala  Val  Glu  Cys  Ile  Glu  Asp  Leu  Leu  Asn  Glu  Pro  Gly
                         220                     225                     230

CAA  CCT  TTG  GAC  TTG  AGC  TGT  AAA  CGC  CCC  AGG  CCATAAGGTG  T                 1000
Gln  Pro  Leu  Asp  Leu  Ser  Cys  Lys  Arg  Pro  Arg  Pro
               235                     240
```

( 2 ) INFORMATION FOR SEQ ID NO:2:

( i ) SEQUENCE CHARACTERISTICS:
        ( A ) LENGTH: 243 amino acids
        ( B ) TYPE: amino acid
        ( D ) TOPOLOGY: linear ( i i ) MOLECULE TYPE: protein ( x i ) SEQUENCE DESCRIPTION: SEQ ID NO:2:

```
Met  Arg  His  Ile  Ile  Cys  His  Gly  Gly  Val  Ile  Thr  Glu  Glu  Met  Ala
 1                    5                    10                        15

Ala  Ser  Leu  Leu  Asp  Gln  Leu  Ile  Glu  Glu  Val  Leu  Ala  Asp  Asn  Leu
               20                        25                   30

Pro  Pro  Pro  Ser  His  Phe  Glu  Pro  Pro  Thr  Leu  His  Glu  Leu  Tyr  Asp
               35                        40                   45

Leu  Asp  Val  Thr  Ala  Pro  Glu  Asp  Pro  Asn  Glu  Glu  Ala  Val  Ser  Gln
          50                        55                   60

Ile  Phe  Pro  Asp  Ser  Val  Met  Leu  Ala  Val  Gln  Glu  Gly  Ile  Asp  Leu
 65                        70                   75                        80

Leu  Thr  Phe  Pro  Pro  Ala  Pro  Gly  Ser  Pro  Glu  Pro  Pro  His  Leu  Ser
                    85                   90                        95

Arg  Gln  Pro  Glu  Gln  Pro  Glu  Gln  Arg  Ala  Leu  Gly  Pro  Val  Ser  Met
                    100                  105                       110

Pro  Asn  Leu  Val  Pro  Glu  Val  Ile  Asp  Leu  Thr  Cys  His  Glu  Ala  Gly
               115                       120                  125

Phe  Pro  Pro  Ser  Asp  Asp  Glu  Asp  Glu  Glu  Gly  Pro  Val  Ser  Glu  Pro
     130                       135                  140

Glu  Pro  Glu  Pro  Glu  Pro  Glu  Pro  Glu  Pro  Ala  Arg  Pro  Thr  Arg  Arg
145                       150                  155                       160

Pro  Lys  Met  Ala  Pro  Ala  Ile  Leu  Arg  Arg  Pro  Thr  Ser  Pro  Val  Ser
                    165                  170                       175

Arg  Glu  Cys  Asn  Ser  Ser  Thr  Asp  Ser  Cys  Asp  Ser  Gly  Pro  Ser  Asn
               180                       185                  190

Thr  Pro  Pro  Glu  Ile  His  Pro  Val  Val  Pro  Leu  Cys  Pro  Ile  Lys  Pro
          195                       200                  205

Val  Ala  Val  Arg  Val  Gly  Gly  Arg  Arg  Gln  Ala  Val  Glu  Cys  Ile  Glu
     210                       215                  220

Asp  Leu  Leu  Asn  Glu  Pro  Gly  Gln  Pro  Leu  Asp  Leu  Ser  Cys  Lys  Arg
225                       230                  235                       240

Pro  Arg  Pro
```

( 2 ) INFORMATION FOR SEQ ID NO:3:

( i ) SEQUENCE CHARACTERISTICS:
        ( A ) LENGTH: 1000 base pairs
        ( B ) TYPE: nucleic acid
        ( C ) STRANDEDNESS: both ( D ) TOPOLOGY: linear ( i i ) MOLECULE TYPE: cDNA ( i i i ) HYPOTHETICAL: NO ( i v ) ANTI-SENSE: NO ( i x ) FEATURE:
    ( A ) NAME/KEY: CDS
    ( B ) LOCATION: join(10..564, 681..993)

( x i ) SEQUENCE DESCRIPTION: SEQ ID NO:3:

```
GGACTGAAA ATG AGA CAT ATT ATC TGC CAC GGA GGT GTT ATT ACC GAA        48
          Met Arg His Ile Ile Cys His Gly Gly Val Ile Thr Glu
            1           5                  10

GAA ATG GCC GCC AGT CTT TTG GAC CAG CTG ATC GAA GAG GTA CTG GCT       96
Glu Met Ala Ala Ser Leu Leu Asp Gln Leu Ile Glu Glu Val Leu Ala
        15                  20                  25

GAT AAT CTT CCA CCT CCT AGC CAT TTT GAA CCA CCT ACC CTT CAC GAA      144
Asp Asn Leu Pro Pro Pro Ser His Phe Glu Pro Pro Thr Leu His Glu
 30                  35                  40                  45

CTG TAT GAT TTA GAC GTG ACG GCC CCC GAA GAT CCC AAC GAG GAG GCG      192
Leu Tyr Asp Leu Asp Val Thr Ala Pro Glu Asp Pro Asn Glu Glu Ala
                 50                  55                  60

GTT TCG CAG ATT TTT CCC GAC TCT GTA ATG TTG GCG GTG CAG GAA GGG      240
Val Ser Gln Ile Phe Pro Asp Ser Val Met Leu Ala Val Gln Glu Gly
             65                  70                  75

ATT GAC TTA CTC ACT TTT CCG CCG GCG CCC GGT TCT CCG GAG CCG CCT      288
Ile Asp Leu Leu Thr Phe Pro Pro Ala Pro Gly Ser Pro Glu Pro Pro
         80                  85                  90

CAC CTT TCC CGG CAG CCC GAG CAG CCG GAG CAG AGA GCC TTG GGT CCG      336
His Leu Ser Arg Gln Pro Glu Gln Pro Glu Gln Arg Ala Leu Gly Pro
     95                 100                 105

GTT TCT ATG CCA AAC CTT GTA CCG GAG GTG ATC GAT CTT ACC TGC CAC      384
Val Ser Met Pro Asn Leu Val Pro Glu Val Ile Asp Leu Thr Cys His
110                 115                 120                 125

GAG GCT GGC TTT CCA CCC AGT GAC GAC GAG GAT GAA GAG GGT GAG GAG      432
Glu Ala Gly Phe Pro Pro Ser Asp Asp Glu Asp Glu Glu Gly Glu Glu
                130                 135                 140

TTT GTG TTA GAT TAT GTG GAG CAC CCC GGG CAC GGT TGC AGG TCT TGT      480
Phe Val Leu Asp Tyr Val Glu His Pro Gly His Gly Cys Arg Ser Cys
            145                 150                 155

CAT TAT CAC CGG AGG AAT ACG GGG GAC CCA GAT ATT ATG TGT TCG CTT      528
His Tyr His Arg Arg Asn Thr Gly Asp Pro Asp Ile Met Cys Ser Leu
        160                 165                 170

TGC TAT ATG AGG ACC TGT GGC ATG TTT GTC TAC AGT AAGTGAAAAT           574
Cys Tyr Met Arg Thr Cys Gly Met Phe Val Tyr Ser
    175                 180                 185

TATGGGCAGT GGGTGATAGA GTGGTGGGTT TGGTGTGGTA ATTTTTTTTT TAATTTTTAC    634

AGTTTGTGG TTTAAAGAAT TTTGTATTGT GATTTTTTA AAAGGT CCT GTG TCT         689
                                                Pro Val Ser

GAA CCT GAG CCT GAG CCC GAG CCA GAA CCG GAG CCT GCA AGA CCT ACC      737
Glu Pro Glu Pro Glu Pro Glu Pro Glu Pro Glu Pro Ala Arg Pro Thr
        190                 195                 200

CGC CGT CCT AAA ATG GCG CCT GCT ATC CTG AGA CGC CCG ACA TCA CCT      785
Arg Arg Pro Lys Met Ala Pro Ala Ile Leu Arg Arg Pro Thr Ser Pro
205                 210                 215                 220

GTG TCT AGA GAA TGC AAT AGT AGT ACG GAT AGC TGT GAC TCC GGT CCT      833
Val Ser Arg Glu Cys Asn Ser Ser Thr Asp Ser Cys Asp Ser Gly Pro
                225                 230                 235

TCT AAC ACA CCT CCT GAG ATA CAC CCG GTG GTC CCG CTG TGC CCC ATT      881
```

-continued

| Ser | Asn | Thr | Pro | Pro | Glu | Ile | His | Pro | Val | Val | Pro | Leu | Cys | Pro | Ile |  |
|---|---|---|---|---|---|---|---|---|---|---|---|---|---|---|---|---|
|   |   |   | 240 |   |   |   | 245 |   |   |   |   | 250 |   |   |   |   |

| AAA | CCA | GTT | GCC | GTG | AGA | GTT | GGT | GGG | CGT | CGC | CAG | GCT | GTG | GAA | TGT | 929 |
|---|---|---|---|---|---|---|---|---|---|---|---|---|---|---|---|---|
| Lys | Pro | Val | Ala | Val | Arg | Val | Gly | Gly | Arg | Arg | Gln | Ala | Val | Glu | Cys |  |
|   |   | 255 |   |   |   |   | 260 |   |   |   | 265 |   |   |   |   |   |

| ATC | GAG | GAC | TTG | CTT | AAC | GAG | CCT | GGG | CAA | CCT | TTG | GAC | TTG | AGC | TGT | 977 |
|---|---|---|---|---|---|---|---|---|---|---|---|---|---|---|---|---|
| Ile | Glu | Asp | Leu | Leu | Asn | Glu | Pro | Gly | Gln | Pro | Leu | Asp | Leu | Ser | Cys |  |
|   | 270 |   |   |   |   | 275 |   |   |   |   | 280 |   |   |   |   |   |

| AAA | CGC | CCC | AGG | CCATAAGGTG | T |  |  |  |  |  |  |  |  |  |  | 1000 |
|---|---|---|---|---|---|---|---|---|---|---|---|---|---|---|---|---|
| Lys | Arg | Pro | Arg | Pro |   |  |  |  |  |  |  |  |  |  |  |   |
| 285 |   |   |   |   |   |  |  |  |  |  |  |  |  |  |  |   |

( 2 ) INFORMATION FOR SEQ ID NO:4:

( i ) SEQUENCE CHARACTERISTICS:
        ( A ) LENGTH: 289 amino acids
        ( B ) TYPE: amino acid
        ( D ) TOPOLOGY: linear ( i i ) MOLECULE TYPE: protein ( x i ) SEQUENCE DESCRIPTION: SEQ ID NO:4:

| Met | Arg | His | Ile | Ile | Cys | His | Gly | Gly | Val | Ile | Thr | Glu | Glu | Met | Ala |
|---|---|---|---|---|---|---|---|---|---|---|---|---|---|---|---|
| 1 |   |   |   | 5 |   |   |   |   | 10 |   |   |   |   | 15 |   |

| Ala | Ser | Leu | Leu | Asp | Gln | Leu | Ile | Glu | Val | Leu | Ala | Asp | Asn | Leu |
|---|---|---|---|---|---|---|---|---|---|---|---|---|---|---|
|   |   |   | 20 |   |   |   |   | 25 |   |   |   |   | 30 |   |

| Pro | Pro | Pro | Ser | His | Phe | Glu | Pro | Pro | Thr | Leu | His | Glu | Leu | Tyr | Asp |
|---|---|---|---|---|---|---|---|---|---|---|---|---|---|---|---|
|   |   | 35 |   |   |   |   | 40 |   |   |   |   | 45 |   |   |   |

| Leu | Asp | Val | Thr | Ala | Pro | Glu | Asp | Pro | Asn | Glu | Glu | Ala | Val | Ser | Gln |
|---|---|---|---|---|---|---|---|---|---|---|---|---|---|---|---|
|   | 50 |   |   |   |   | 55 |   |   |   |   | 60 |   |   |   |   |

| Ile | Phe | Pro | Asp | Ser | Val | Met | Leu | Ala | Val | Gln | Glu | Gly | Ile | Asp | Leu |
|---|---|---|---|---|---|---|---|---|---|---|---|---|---|---|---|
| 65 |   |   |   |   | 70 |   |   |   |   | 75 |   |   |   |   | 80 |

| Leu | Thr | Phe | Pro | Pro | Ala | Pro | Gly | Ser | Pro | Glu | Pro | Pro | His | Leu | Ser |
|---|---|---|---|---|---|---|---|---|---|---|---|---|---|---|---|
|   |   |   |   | 85 |   |   |   |   | 90 |   |   |   |   | 95 |   |

| Arg | Gln | Pro | Glu | Gln | Pro | Glu | Gln | Arg | Ala | Leu | Gly | Pro | Val | Ser | Met |
|---|---|---|---|---|---|---|---|---|---|---|---|---|---|---|---|
|   |   |   | 100 |   |   |   |   | 105 |   |   |   |   | 110 |   |   |

| Pro | Asn | Leu | Val | Pro | Glu | Val | Ile | Asp | Leu | Thr | Cys | His | Glu | Ala | Gly |
|---|---|---|---|---|---|---|---|---|---|---|---|---|---|---|---|
|   |   | 115 |   |   |   |   | 120 |   |   |   |   | 125 |   |   |   |

| Phe | Pro | Pro | Ser | Asp | Asp | Glu | Asp | Glu | Glu | Gly | Glu | Glu | Phe | Val | Leu |
|---|---|---|---|---|---|---|---|---|---|---|---|---|---|---|---|
|   | 130 |   |   |   |   | 135 |   |   |   |   | 140 |   |   |   |   |

| Asp | Tyr | Val | Glu | His | Pro | Gly | His | Gly | Cys | Arg | Ser | Cys | His | Tyr | His |
|---|---|---|---|---|---|---|---|---|---|---|---|---|---|---|---|
| 145 |   |   |   |   | 150 |   |   |   |   | 155 |   |   |   |   | 160 |

| Arg | Arg | Asn | Thr | Gly | Asp | Pro | Asp | Ile | Met | Cys | Ser | Leu | Cys | Tyr | Met |
|---|---|---|---|---|---|---|---|---|---|---|---|---|---|---|---|
|   |   |   |   | 165 |   |   |   |   | 170 |   |   |   |   | 175 |   |

| Arg | Thr | Cys | Gly | Met | Phe | Val | Tyr | Ser | Pro | Val | Ser | Glu | Pro | Glu | Pro |
|---|---|---|---|---|---|---|---|---|---|---|---|---|---|---|---|
|   |   |   |   | 180 |   |   |   |   | 185 |   |   |   |   | 190 |   |

| Glu | Pro | Glu | Pro | Glu | Pro | Glu | Pro | Ala | Arg | Pro | Thr | Arg | Arg | Pro | Lys |
|---|---|---|---|---|---|---|---|---|---|---|---|---|---|---|---|
|   |   |   | 195 |   |   |   |   | 200 |   |   |   |   | 205 |   |   |

| Met | Ala | Pro | Ala | Ile | Leu | Arg | Arg | Pro | Thr | Ser | Pro | Val | Ser | Arg | Glu |
|---|---|---|---|---|---|---|---|---|---|---|---|---|---|---|---|
|   |   | 210 |   |   |   |   | 215 |   |   |   |   | 220 |   |   |   |

| Cys | Asn | Ser | Ser | Thr | Asp | Ser | Cys | Asp | Ser | Gly | Pro | Ser | Asn | Thr | Pro |
|---|---|---|---|---|---|---|---|---|---|---|---|---|---|---|---|
| 225 |   |   |   |   | 230 |   |   |   |   | 235 |   |   |   |   | 240 |

| Pro | Glu | Ile | His | Pro | Val | Val | Pro | Leu | Cys | Pro | Ile | Lys | Pro | Val | Ala |
|---|---|---|---|---|---|---|---|---|---|---|---|---|---|---|---|
|   |   |   |   | 245 |   |   |   |   | 250 |   |   |   |   | 255 |   |

-continued

| Val | Arg | Val | Gly | Gly | Arg | Arg | Gln | Ala | Val | Glu | Cys | Ile | Glu | Asp | Leu |
|---|---|---|---|---|---|---|---|---|---|---|---|---|---|---|---|
| | | | 260 | | | | | 265 | | | | | 270 | | |
| Leu | Asn | Glu | Pro | Gly | Gln | Pro | Leu | Asp | Leu | Ser | Cys | Lys | Arg | Pro | Arg |
| | | 275 | | | | | 280 | | | | | 285 | | | |
| Pro | | | | | | | | | | | | | | | |

METHOD OF SENSITIZING TUMOR CELLS WITH ADENOVIRUS E1A

The present invention was made with support in part from a National Institutes of Health Grant R29GM44573-05. The United States Government may have certain rights in the invention.

BACKGROUND OF THE INVENTION

1. Field of the Invention

This invention relates generally to the fields of molecular biology and more specifically to the effect of adenovirus E1A on tumor cells.

2. Background Information

Both radiation and chemotherapy have significantly contributed to the treatment of cancer. However, impediments to successful therapy by either form of treatment still remain. For example, some tumor types fail to respond to either radiation or chemotherapy. In other instances, originally responsive malignant cells may experience a relapse and become resistant to treatment.

There is evidence that the expression of certain proteins, such as various oncogenes, can increase the susceptibility of cells to apoptosis, also known as programmed cell death. Further, there is evidence that some of these proteins may also confer susceptibility to apoptosis induced by anticancer agents. However, relatively few studies have been done to observe these effects on human tumor cells and there have been no reports on the effect of adenovirus E1A on the sensitivity of human tumor cells and the response of these E1A-expressing cells to chemotherapeutic agents or irradiation.

Given the shortcomings of current chemotherapy and irradiation, namely lack of response and resistance or tolerance to chemotherapy agents, there is a need for developing additional forms of treatment which can enhance a response to chemotherapy or irradiation.

The present invention satisfies these needs and provides related advantages as well. The present invention provides novel methods for treating a tumor cell and enhancing a patient's response to irradiation and chemotherapy.

SUMMARY OF THE INVENTION

The present invention is directed to methods of sensitizing a human tumor cell with adenovirus E1A. The methods involve treating a human tumor cell by, first, introducing into the tumor cell nucleic acid encoding a polypeptide having adenovirus E1A activity, expressing the E1A active polypeptide in the cell, and then either contacting the E1A expressing tumor cell with a chemotherapeutic agent or irradiating the E1A-expressing tumor cell.

The invention also provides methods of enhancing a subject's response to chemotherapy or irradiation by introducing into a subject's tumor cells nucleic acid encoding a polypeptide having adenovirus E1A activity, expressing the E1A active polypeptide in the cells and finally, administering either a chemotherapeutic agent or irradiation. This invention also provides a method of treating cancer.

BRIEF DESCRIPTION OF THE DRAWINGS

FIG. 5A to 5C provides the DNA sequence of E1A coding sequences (cDNA). Bottom line: 243 amino acid sequence. Top line: 289 amino acid sequence.

DETAILED DESCRIPTION OF THE INVENTION

Figure 1:
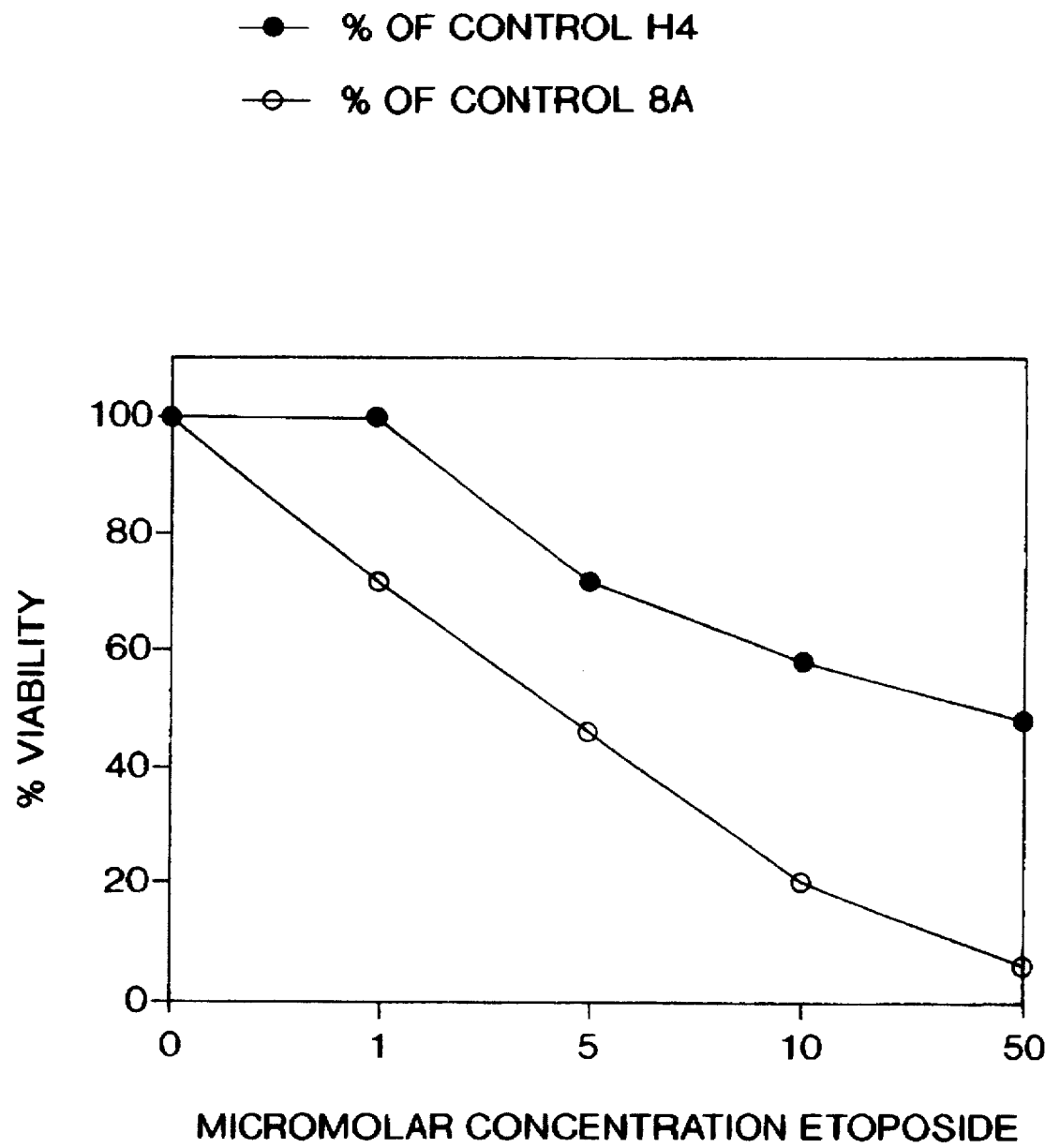
FIG. 1 graphs the effect of E1A-expressing human HT1080 fibrosarcoma cells to etoposide. Comparisons were made in a dose response assay at the indicated etoposide dosages of parental HT1080 fibrosarcoma cells lacking E1A (H4) and HT1080 fibrosarcoma cells expressing E1A (8A). Results reported as percent viability of the cells compared to dose of etoposide.

Adenovirus is a large DNA virus whose natural host is human cells. Virtually every adult has been infected with adenovirus at some time, the major effect being cold-like symptoms. Adenovirus is referred to as a "DNA tumor virus" because of its oncogenic effect in rodents. Expression of the adenovirus genome occurs in two stages. First, the early gene products are expressed which encode the E1A and the E1B genes. These products are necessary for expression of the gate gene products. Late gene products encode proteins necessary for replication as well as the viral structural proteins.

The proteins encoded by the E1A gene of adenovirus have been studied primarily from two points of view. First, the 243 amino acid and 289 amino acid forms of E1A (arising from alternative splicing of the precursor RNA such that the 243 amino acid protein is a subset of the 289 amino acid protein) are both transcriptional regulatory proteins. J. Flint, T. Shenk, *Ann. Rev. Gen.*, 23:141–161 (1989). Secondly, these proteins facilitate the oncogenic transformation of certain rodent cells by other oncogenes. H. E. Ruley, *Nature*, 304:602–606 (1983), and, as such E1A is generally classified as an oncogene.

There is evidence t hat the expression of oncogenes can increase the susceptibility of cells to apoptosis, also known as programmed cell death. Lowe et al., *Cell*, 74:957–967 (1993). For example, the E1A gene may increase cellular susceptibility to apoptosis in primary rodent cells. Roa et al, *Proc. Natl. Acad. Sci.*, 89:7742–7746 (1992). Other oncogenes, such as c-myc, can also increase cellular susceptibility to programmed cell death. Evan et al., *Cell*, 69:119–128 (1992), and overexpression of c-myc may also confer susceptibility to apoptosis induced by anticancer agents, such as tumor necrosis factor α, Chen et al., *Nature*, 330:581–583 (1987), or etoposide. Fanidi et al., *Nature*, 359:554–556 (1992) and Lowe et al., supra. Additionally, Lowe et al., supra, explore the effects of p53 in combination with E1A on the sensitivity of mouse embryo fibroblasts (MEFs) to chemotherapeutic drugs.

Interestingly, and in contrast to E1A's oncogenic and apoptotic effects in rodent cells, E1A acts as a tumor suppressor gene in the human context. Steven M. Frisch,

*Proc. Natl. Acad. Sci.*, 88:9077-9081 (1991), which is incorporated herein by reference, provides evidence of the antioncogenic effect of adenovirus E1A in human tumor cells. More importantly, it is striking and unexpected that E1A, sensitizes human tumor cells and enhances tumor cell's response to chemotherapy and irradiation treatment. The effect is independent of p53.

These unexpected observations provide the basis for this invention, which is directed to methods of sensitizing a human tumor cell with adenovirus E1A. The methods involve treating a human tumor cell by, first, introducing into the tumor cell nucleic acid encoding a polypeptide having adenovirus E1A activity, expressing the E1A active polypeptide in the cell, and then either contacting the E1A-expressing tumor cell with a chemotherapeutic agent or irradiating the E1A-expressing tumor cell. The methods may be practiced in vitro or in vivo.

Also provided by this invention are methods of enhancing a subject's response to chemotherapy or irradiation by introducing into a subject's tumor cells nucleic acid encoding a polypeptide having adenovirus E1A activity, expressing the E1A active polypeptide in the cells and finally, administering either a chemotherapeutic agent or irradiation.

The invention also provides methods of treating a cancer which is susceptible to treatment by introducing into a subject's tumor cells nucleic acid encoding a polypeptide having adenovirus E1A activity, expressing said polypeptide in said tumor cells, and finally, either contacting said tumor cells with a chemotherapeutic agent or irradiating said tumor cells.

Treating human tumor cells with E1A sensitizes the cells. The sensitization results in enhancing a tumor cell's susceptibility to respond to chemotherapeutic agents or irradiation. As evidenced in the ensuing Examples, by the instant methods E1A-expressing cells more readily sensitize human tumor cells and make them more susceptible to killing by, chemotherapy or irradiation as compared to cells lacking E1A. Of course, it will be understood that chemotherapeutic agents or irradiation may affect tumor cells by a variety of ways, including killing or decreased viability, by for example apoptosis or other mechanisms, poisoning, inactivation of tumor, and the like. It is expected, regardless of the mechanisms by which the toxic agents (chemotherapeutic agents or irradiation) work, E1A-expression sensitizes the cells and enhances their response to chemotherapy or irradiation. While not wishing to be bound by any theory or mechanism, it is postulated that the instant invention may work based on E1A's ability to reverse-transform human tumor cells and convert them to epithelial cells. Reverse-transformation by E1A confers sensitivity to anoikis (a type of programmed cell death). Frisch and Francis, *J. Cell Biology*, 124:619-626 (February 1994).

One can easily test for sensitization by assays well known and readily available in the art, such as for example by a dose response assay to assess cell niability or agarose gel electrophoresis of DNA extractions to determine DNA fragmentation, a characteristic of cell death. Both of these assays are further described in the Examples below. Other assays, such as a chromatin assay, which is well known in the art, or drug resistance assays (as described, for example, in Lowe et al., *Cell*, 74:957-967 (1993), which is incorporated herein by reference) may also be used to determine the effect of E1A on the sensitivity of tumor cells and their response to E1A and chemotherapy agents or irradiation.

As used herein, the term "nucleic acid" means DNA, including cDNA, or RNA. Isolated nucleic acids useful in this invention are those that encode a polypeptide functionally equivalent to a polypeptide encoded by the E1A region of the adenovirus genome. In one aspect of this invention, the isolated nucleic acid is the adenovirus E1A region. This region is defined by those of skill in the art to be from nucleotide 560 to nucleotide 1542. The nucleotide and amino acid sequence of E1A is provided in FIG. 5.

As used herein, the term "introducing" in relation to nucleic acid encompasses any method of inserting an exogenous nucleic acid molecule into a cell and includes, but is not limited to transduction, transfection, microinjection and viral infection of host cells. Methods of carrying out these procedures are well known to those of skill in the art. The nucleic acid may be introduced, for example, by contacting the cell with an adenovirus vector or a retroviral vector. In a preferred embodiment, the nucleic acid is introduced into the cell by contacting a cell with a retroviral vector containing the nucleic acid under conditions such that the nucleic acid is inserted into the cell. In the most preferred embodiment of this invention, the virus is a replication-incompetent retrovirus. A replication-incompetent retrovirus is defined as a virus not having the ability to produce viral proteins, precluding spread of the vector in the infected host cells. Examples of such vectors useful for the practice of this invention are well known and readily available to those of skill in the art.

The E1A gene product has the capacity, after being expressed in a human tumor cell to sensitize the tumor cell and enhance the cell's response to a chemotherapeutic agent or irradiation. Such capacity is herein termed "E1A activity." A "polypeptide having E1A activity" is used in its broadest sense to include the structure of native adenovirus E1A, its functional subunits and fragments and modifications to the native sequence which retain E1A activity. In one aspect of the invention, this amino acid sequence is the 243 amino acid polypeptide product of the adenovirus E1A gene, as provided in FIG. 5. Functional equivalents of the 243 amino acid polypeptide are polypeptides that can also sensitize human tumor cells and enhance their susceptibility to treatment by chemotherapy agents or irradiation. Cells which express a polypeptide having E1A activity are repeatedly referred to herein as "E1A-expressing" cells. The activity of an E1A polypeptide can be routinely determined by any one of the tests for sensitivity and/or response to cancer treatment as described above and below.

The invention relates generally to a method of sensitizing a human tumor cell based on the effect of E1A and the response of E1A-expressing cells to a toxic agent, i.e., chemotherapeutic agent or irradiation. As used herein, the phrase "chemotherapeutic agent" means any chemical agent or drug used in chemotherapy treatment which selectively affects tumor cells, including but not limited to such agents as adriamycin, amsacrine, etoposide, cisplatinum, vincristine, vinblastine, methotrexate. Other such agents are well known in the art. As described above, the agents encompassed by this invention are not limited to working by any one mechanism, and may for example be effective by direct poisoning, apoptosis or other mechanisms of cell death or killing, tumor inactivation, or other mechanisms known or unknown. The means for contacting tumor cells with these agents and for administering a chemotherapeutic agent to a subject are well known and readily available to those of skill in the art.

As used herein, the term "irradiation" or "irradiating" is intended in its broadest sense to include any treatment of a tumor cell or subject by photons, electrons, neutrons or other ionizing radiations. These radiations include, but are not limited to, X-rays, gamma-radiation, or heavy ion particles, such as alpha or beta particles. Moreover, the irradiation may be radioactive, as is commonly used in cancer treatment and can include interstitial irradiation. The means for irradiating tumor cells and a subject are well known and readily available to those of skill in the art.

The methods described herein can be useful for sensitizing cancers of a number of types, including but not limited to breast cancer, sarcomas and other neoplasms, bladder cancer, colon cancer, lung cancer, various leukemias and lymphomas. The tumor cells of the instant invention are from human tumors or malignancies. In one aspect of this invention, human tumor cells do not express functional p53. Human tumor cells which do not express functional p53, include, but are not limited to, HT1080 fibrosarcoma, Saos2 osteosarcoma, NCI-H23 non-small cell lung carcinoma, and RD rhabdomyosarcoma. Evidence that these cell types do not express functional p53 can be found as follows: HT1080: Anderson et al., *Genes, Chromosomes & Cancer*, 9:266–281 (1994), which is incorporated herein by reference; Saos-2: Subler and Martin, *J. of Virology*, 68:103–110 (1994), which is incorporated herein by reference; RD: Felix et al., *Cancer Research*, 52:2243–2247 (1992), which is incorporated herein by reference; and NCI-H23: Takahashi et al., *Cancer Research*, 52:2340–2343 (1992), which is incorporated herein by reference. One would expect that any other human tumor cell and particularly ones which do not express functional p53 would be sensitized by E1A and would enhance the cells' response to chemotherapeutic drugs or irradiation.

The phrase "functional p53" means any structure which substantially corresponds to the native p53 protein and which has the function of native p53, which is generally known to be tumor suppression. Therefore, mutations in p53 which result in a lack of p53 activity or function would not be encompassed by "functional p53." One can readily determine by routine and well known procedures whether or not a cell is expressing p53 at all. Further, one can readily determine by the same or similar known procedures, if a cell is expressing p53, whether it is functional p53 or a mutated, non-functional version of p53.

Presumptive evidence for the presence of mutant, non-functional p53 can be obtained, for example, by Western blot analysis using monoclonal antibody PAb1801 (Oncogene Science; New York). Such an assay capitalizes on the fact that mutant forms of p53 are more stable than wild-type (functional) p53 and therefore accumulate to much higher protein levels than wild-type p53. Parental cell lines, such as HT1080 cells can be used as a positive control and FM 0097 cells, for example, can be used as a negative control. These materials and methods are described in Anderson et al., supra, which is incorporated herein by reference. The presence of wild-type or non-functional mutant forms of p53 can be confirmed by preparing a p53 cDNA clone from the chosen cell line, followed by determining its primary DNA sequence using standard methods well known and available in the art.

The invention also provides methods of enhancing a subject's response to chemotherapy or irradiation by introducing into a subject's tumor cells nucleic acid encoding a polypeptide having adenovirus E1A activity, expressing the E1A active polypeptide in the cells and finally, administering either a chemotherapeutic agent or irradiation.

For enhancing a subject's response to chemotherapy or irradiation, a population of tumor cells can be isolated by a variety of procedures known to those skilled in the art.

Isolation is most commonly done surgically by a biopsy. After introduction and expression of E1A in the cells, the new population of E1A-expressing cells are then transferred back into the subject, generally by reinjection or other means well known in the field. Thereafter, tumor regression and/or progression can be monitored by standard methodologies known in the art.

The following examples are intended to illustrate but not limit the invention.

EXAMPLE I

MATERIALS AND METHODS

Stable E1A-expressing cell lines from HT1080 fibrosarcoma cells and A2058 melanoma cells were constructed using the plasmid p1Aneo as described in Frisch et al., *Oncogene* 5:75–83 (1990), which is incorporated herein by reference, Franza et al., *Cell*, 44:408–418 (1988), which is incorporated herein by reference, and Maruyama et al., *Oncogene* 1:361–367 (1987), which is incorporated herein by reference. Cells labeled HT1080neo' and A2058neo' resulted from transfection with Bluescript plasmid (Stratagene, La Jolla, Calif.) containing the simian virus 40 early enhancer-promoted aph gene (encoding resistance to G418).

Figure 3A:
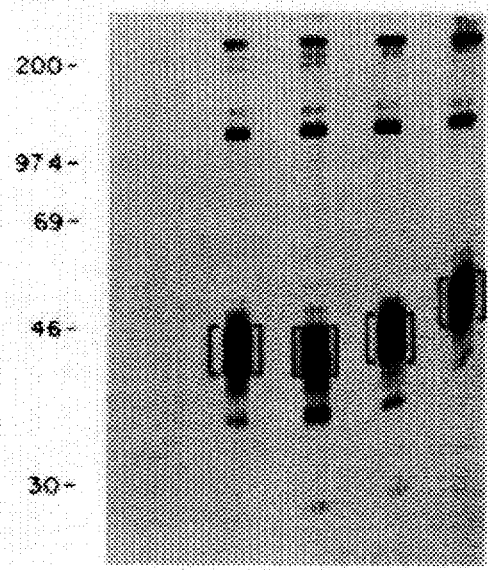
FIGS. 3A and 3B provides evidence of stable transfection and expression of E1A in various tumor cells by immunoprecipitation of E1A proteins from stably transfected and parental cell lines. The bands corresponding to E1A protein species are bracketed.
Figure 3B:
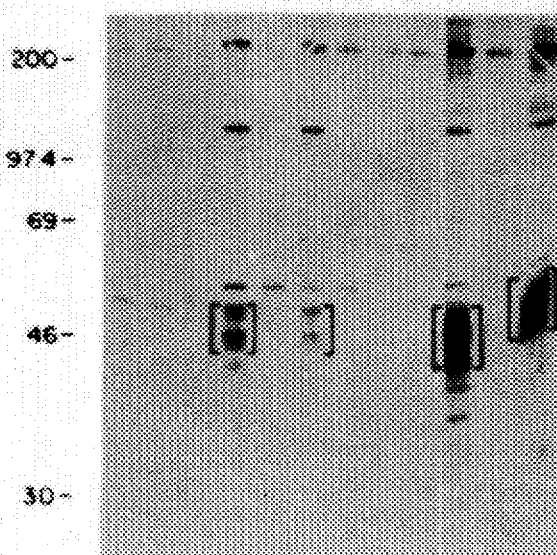

The expression of the E1A gene was documented at the RNA level by Northern blot analysis, also as described in Frisch et al., supra. Protein expression was further documented by immunoprecipitation with E1A-specific monoclonal antibodies as follows. Confluent cultures of cell lines (containing $2 \times 10^6$ cells) were labeled for 5 hours in 35-mm wells with 0.4 mCi (1 Ci=37 GBq) of [$^{35}$S]methionine (Tran$^{35}$S-label, ICN) in methionine-free Dulbecco's modified Eagle's medium containing 5% (vol/vol) dialyzed fetal calf serum. Cells were washed twice in phosphate-buffered saline and scraped into 1.0 ml of RIPA-1 [50 mM Tris-HCl, pH 7.5/0.1% Nonidet P-40/250 mM NaCl/aprotinin (10 µg/ml) leupeptin (5 µg/ml)1 mM phenylmethylsulfonyl fluoride/5 mM EDTA/soybean trypsin inhibitor (10 µg/ml)]. After addition of bovine serum albumin to 0.5 mg/ml, lysates were preabsorbed with 100 µl of a 50% (wt/vol) protein A-Sepharose (Pharmacia; Indianapolis, Ind.) slurry (prepared in RIPA-1 containing bovine serum albumin at 0.5 mg/ml) by mixing at 4° C. for 30 minutes and centrifuging for 10 minutes at 14,000 rpm in an Eppendorf microcentrifuge and 0.5 ml samples were then incubated with 1.5 µg of anti-E1A monoclonal antibody M73 Harlow et al., *J. Virol.*, 3:533–546 (1985) or control antibody [anti-fos Ab-1 (Oncogene Sciences, Mineola, N.Y.)] for 2 hours at 0° C. Then 25 µl of 50% protein A-Sepharose slurry was added and the tubes were mixed for 20 minute at 4° C. followed by a 2-minutes centrifugation and five 0.5 ml washes with RIPA-1. Pellets were then resuspended in 60 µl of sample buffer and analyzed with SDS/PAGE. E1A protein was detected on the gel as evidenced by FIG. 3 which shows the [35S]methionine-labeled proteins from E1A-expressing clones derived from HT1080 cells (lanes 1–5), HeLa cells (lanes 6–8), and A2058 cells (lanes 9–11) immunoprecipitated with anti-E1A antibodies (E) or control antibodies (C). Lanes: 1–5, HT1080, p2AHT2a, p1Aneo3, p1Aneo15, and p1Aneo16, respectively: 6–8, HeLa, Medg18, and Medg28, respectively: 9–11, A2058, 1A58c8-1, and 1A58c11-1, respectively. The bands corresponding to E1A protein species are bracketed.

Figure 4:
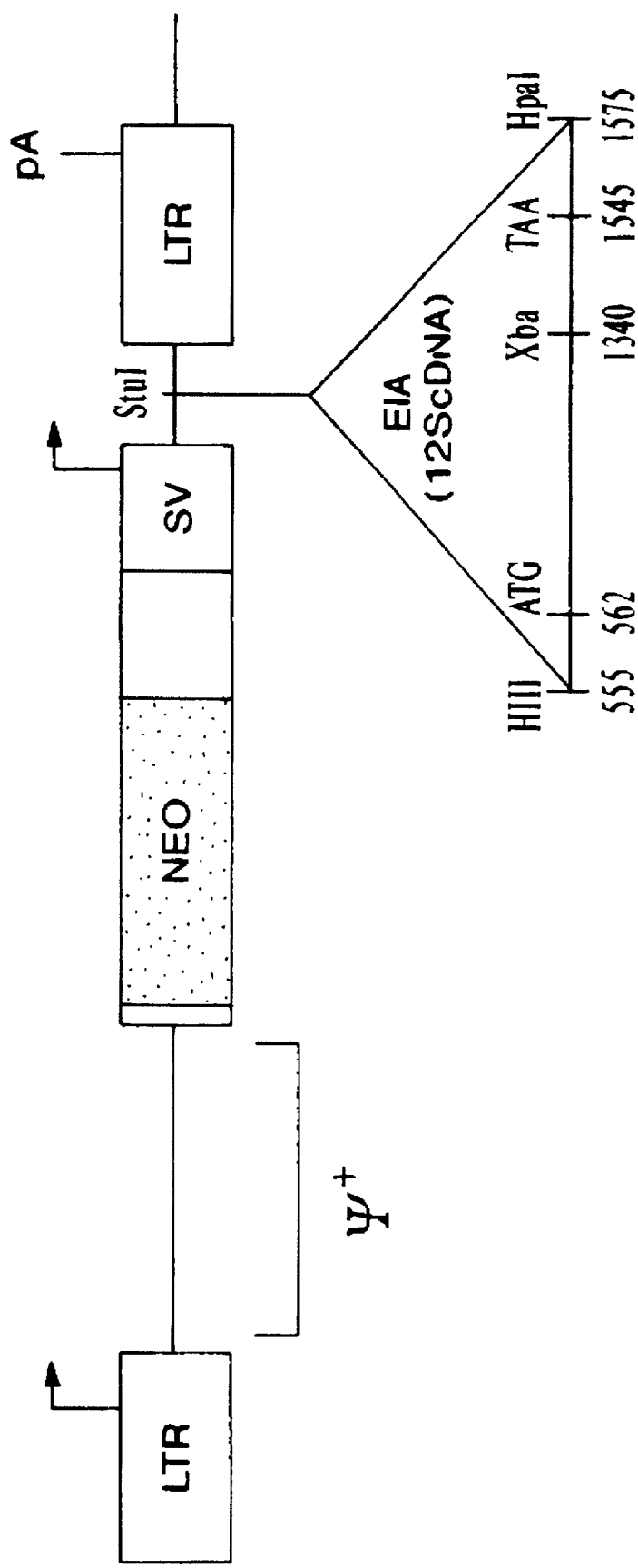
FIG. 4 depicts the structure of an E1A reverse-transforming retrovirus construct.

In addition, construction of E1A viral expression vectors was achieved by subcloning cDNAs encoding the 243 amino acid or 289 amino acid E1A proteins of adenovirus type 5 into the retroviral vectors: LNCX, LNSX. The 243 amino acid form of E1A (12S cDNA) was cut at adenovirus map position 610 with BstX1 and the 5' end was reconstructed with a double-stranded oligonucleotide, thus removing all E1A 5' noncoding sequences. The HindIII end of this oligonucleotide was made blunt ended and the 3' end of E1A was cut with HpaI (map position 1575) to remove the polyA addition site. The resulting E1A sequence was subcloned into the retrovirus vector LNSX (described in Miller and Rosman, *Biotechniques* 7:980–990 (1989), which is incorporated herein by reference, the retroviral plasmid construct is schematically depicted in FIG. 4).

Ten µg of these plasmid DNAs were transfected into the ecotropic packaging cell line gpE86 (maintained in hygromycin/mycophenolic acid selection medium). At 48 hours post transfection, unselected virus stocks were prepared by collecting conditioned media, clearing by centrifugation and freezing. These viral stocks were used to infect the amphotropic packaging cell line gpEam12 (cells available from ATCC) in 35 mm wells by incubation for 12 hours in DME/10% fetal calf serum media containing 4 µg/ml polybrene. At 24 hours post-infection, cells were split at ratios between 1:100–1:300, and infected cells were selected in 500 µg/ml G418 for 3 weeks. Virus-producing cell lines were expanded into 35 mm wells and conditioned media containing virus was prepared for each line. Virus stocks were prepared from producer cell lines containing either 243 amino acid E1A or 289 amino acid E1A, in the vectors LNCX and LNSX (which promote transcription using internal CMV or SV40 early enhancers, respectively).

Figure 6:
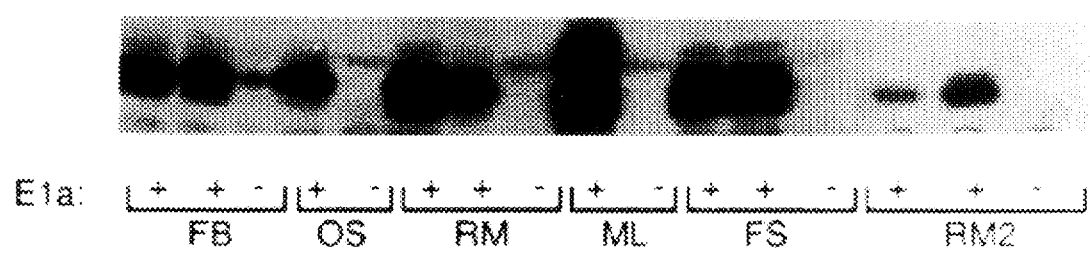
FIG. 6 provides evidence of E1A protein expression in HT1080 fibrosarcoma (FS), E1A+ derivative cells as compared to the parental HT1080 cell line (E1A−).

These stocks were used to infect the human fibrosarcoma line HT1080 by incubating 0.4 ml of virus stock with a 35 mm well of HT1080 cells for 8 hours in medium containing polybrene; infected cells were split at various ratios 24 hours post-infection, and either G418-resistant clones or mixed populations of infected cells were analyzed further. These materials and methods of infecting HT1080 cells with E1A retroviral vectors are also described in Frisch and Francis, J. Cell Biology, 124:619–626 (1994), which is incorporated herein by reference. The E1A protein expression was confirmed by Western blot analysis as shown in FIG. 6 (HT1080 fibrosarcoma (FS) cells expressing E1A (E1A+) compared to HT1080 parental subclone (E1A–)).

EXAMPLE II

EFFECT OF E1A ON THE SENSITIVITY OF HUMAN FIBROSARCOMA CELLS

This example demonstrates the effect of E1A on the sensitivity of HT1080 human fibrosarcoma cells and the E1A-expressing cell's response to etoposide.

The parental HT1080-derived subclone cells (H4) lacking E1A and the HT1080 fibrosarcoma cells expressing E1A (8A) which was prepared by the above method of infection with a retroviral vector were plated in 35 mm diameter wells and grown to 70% confluence. Doses of etoposide (Sigma, St. Louis, Miss.; 1, 5, 10, and 50 micromolar concentrations) were added to the plates and the cells were incubated for an additional 13 hours. After trypsinization, viable cell numbers were determined by staining with trypan blue (Sigma, St. Louis, Miss.) and counting in a hemacytometer. Percent survival (viability) was calculated and graphed relative to the given dose (FIG. 1).

As shown in FIG. 1, E1A enhances the sensitivity of the fibrosarcoma cells and response to the chemotherapeutic agent etoposide, killing significantly more cells than the parental HT1080 cells which lack E1A. Because HT1080 cells do not express functional p53, Anderson et al., *Genes, Chromosomes & Cancer*, 9:266–281 (1994), the observed effect of enhanced sensitization is independent of the p53 protein.

EXAMPLE III

EFFECT OF E1A ON THE SENSITIVITY OF HUMAN MELANOMA CELLS

This example demonstrates the effect of E1A on the sensitivity of A2058 human melanoma cells and the E1A-expressing cell's response to etoposide.

Parental A2058 human melanoma cells lacking E1A (E1A–) and the E1A-expressing derivative cell line 1A58c8-1 (E1A+) both were plated in 60 mm dishes and grown to confluence. Etoposide (Sigma, St. Louis, Miss.) was added to a final concentration of 25 µM and incubation was continued for another 24 hours. Low-molecular weight DNA was extracted with 0.5% Triton X-100, 10 mM EDTA, and 10 mM Tris, pH 7.4 (0.6 ml), phenol-chloroform extracted three times, ethanol precipitated and analyzed on a 1.5% agarose gel in TBE buffer.

Figure 2:
FIG. 2 shows the effect of E1A-expressing human A2058 melanoma cells to etoposide. Comparisons were made by agarose gel electrophoresis of DNA extracted from A2058 melanoma cells in the absence (−) or presence (+) of E1A and the absence (−) or presence (+) of etoposide.

As demonstrated in FIG. 2, there is no DNA degradation, indicative of cell death, in cells lacking E1A, even where etoposide is present (E1A–, etoposide–; E1A–, etoposide+). And while there is evidence of some DNA degradation and killing with E1A alone (E1A+, etoposide–), with the methods of this invention there is a striking increase in DNA degradation and hence the response of human melanoma cells to etoposide in the presence of E1A (E1A+; etoposide+).

Although the invention has been described with reference to the disclosed embodiments, those skilled in the art will readily appreciate that the specific examples detailed are only illustrative of the invention. It should be understood that various modifications can be made without departing from the spirit of the invention. Accordingly, the invention is limited only by the following claims.

I claim:

1. A method of treating a human tumor cell, comprising the steps of:
   a. introducing in vitro into a tumor cell which does not express functional p53, nucleic acid encoding a polypeptide having E1A activity, said polypeptide derived from a type 5 adenovirus;
   b. expressing said polypeptide in said tumor cell;
   c. contacting said tumor cell with a chemotherapeutic agent; and
   d. enhancing the sensitivity of said tumor cell expressing said polypeptide to said chemotherapeutic agent.

2. The method of claim 1, wherein the nucleic acid encodes adenovirus E1A polypeptide (SEQ ID NO: 2).

3. The method of claim 1, wherein the nucleic acid is introduced into the tumor cell by contacting the cell with a suitable retroviral vector containing the nucleic acid sequence.

4. A method of claim 1, wherein the chemotherapeutic agent is selected from the group consisting of etoposide, adriamycin, amsacrine, actinomycin D, VP16, camptothecin, colchicine, taxol, cisplatinum, vincristine, vinblastine, and methotrexate.

5. A method of treating a human tumor cell, comprising the steps of:
   a. introducing in vitro into a tumor cell which does not express functional p53, nucleic acid encoding a polypeptide having E1A activity, said polypeptide derived from a type 5 adenovirus;
   b. expressing said polypeptide in said tumor cell;
   c. irradiating said tumor cell; and
   d. enhancing the sensitivity of said tumor cell expressing said polypeptide to said irradiation.

6. The method of claim 5, wherein the nucleic acid encodes adenovirus E1A polypeptide (SEO ID NO: 2).

7. The method of claim 5, wherein the nucleic acid is introduced into the tumor cell by contacting the cell with a suitable retroviral vector containing the nucleic acid sequence.

* * * * *

UNITED STATES PATENT AND TRADEMARK OFFICE
CERTIFICATE OF CORRECTION

PATENT NO. : 5,776,743
DATED : Jul. 7, 1998
INVENTOR(S) : Steven M. Frisch

It is certified that error appears in the above-identified patent and that said Letters Patent is hereby corrected as shown below:

In column 2, line 34, please delete "gate" and replace therefor with --late--.

In column 2, line 55, please delete "c-myc" and replace therefor with --*c-myc*--.

In column 2, line 57, please delete "c-myc" and replace therefor with --*c-myc*--.

In column 3, line 56, please delete "niability" and replace therefor with --viability--.

In column 4, line 53, after "etoposide," please insert --actinomycin D, VP 16, camptothecin, colchicine, taxol,--.

In column 6, line 18, please delete "*Oncogene*" and replace therefor with --*Oncogene,*--.

UNITED STATES PATENT AND TRADEMARK OFFICE
CERTIFICATE OF CORRECTION

PATENT NO. : 5,776,743
DATED : Jul. 7, 1998
INVENTOR(S) : Steven M. Frisch

It is certified that error appears in the above-identified patent and that said Letters Patent is hereby corrected as shown below:

In column 6, line 53, please delete "2-minutes" and replace therefor with --2 minute--.

In column 8, line 4, please delete "Miss.;" and replace therefor with --MO;--.

In column 8, line 8, please delete "Miss.;" and replace therefor with --MO;--.

In column 8, line 32, please delete "Miss.;" and replace therefor with --MO;--.

UNITED STATES PATENT AND TRADEMARK OFFICE
CERTIFICATE OF CORRECTION

PATENT NO. : 5,776,743
DATED : July 7, 1998
INVENTOR(S) : Steven M. Frisch

Page 3 of 3

It is certified that error appears in the above-identified patent and that said Letters Patent is hereby corrected as shown below:

In column 18, line 25, please delete "(SEO" and replace therefor with --(SEQ--.

Signed and Sealed this

Tenth Day of October, 2000

Attest:

Attesting Officer

Q. TODD DICKINSON

Director of Patents and Trademarks